(12) United States Patent
Dodde et al.

(10) Patent No.: US 7,815,641 B2
(45) Date of Patent: Oct. 19, 2010

(54) SURGICAL INSTRUMENT AND METHOD FOR USE THEREOF

(75) Inventors: Robert Dodde, Ann Arbor, MI (US);
Albert J. Shih, Ann Arbor, MI (US);
James Geiger, Ann Arbor, MI (US);
William Roberts, Saline, MI (US);
Kevin Pipe, Ann Arbor, MI (US);
Arnold Advincula, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 762 days.

(21) Appl. No.: 11/626,812

(22) Filed: Jan. 24, 2007

(65) Prior Publication Data

US 2007/0179489 A1    Aug. 2, 2007

Related U.S. Application Data

(60) Provisional application No. 60/761,901, filed on Jan. 25, 2006.

(51) Int. Cl.
*A61B 18/14* (2006.01)
(52) U.S. Cl. .............................. 606/51; 606/20; 606/22; 606/41; 606/48; 606/52
(58) Field of Classification Search ................... 606/48, 606/50–52, 20–26
See application file for complete search history.

(56) References Cited

U.S. PATENT DOCUMENTS

| | | | |
|---|---|---|---|
| 5,599,350 A | 2/1997 | Schulze et al. | |
| 5,647,871 A * | 7/1997 | Levine et al. | 606/45 |
| 5,964,758 A * | 10/1999 | Dresden | 606/45 |
| 6,033,399 A | 3/2000 | Gines | |
| 6,443,970 B1 | 9/2002 | Schulze et al. | |
| 6,458,128 B1 | 10/2002 | Schulze | |
| 6,464,702 B2 | 10/2002 | Schulze et al. | |
| 6,547,786 B1 | 4/2003 | Goble | |
| 6,554,829 B2 | 4/2003 | Schulze et al. | |
| 6,620,161 B2 | 9/2003 | Schulze et al. | |

(Continued)

OTHER PUBLICATIONS

International Search Report and Written Opinion for PCT/US07/61056 dated Oct. 4, 2007.

*Primary Examiner*—Linda C Dvorak
*Assistant Examiner*—Jaymi Della
(74) *Attorney, Agent, or Firm*—Brooks Kushman P.C.

(57) ABSTRACT

A surgical instrument for treating a tissue includes a handpiece and a tissue engaging portion arranged to be received by the handpiece. The tissue engaging portion includes first and second opposed jaw members having an open position and a closed position for engaging the tissue therebetween, where the first and second jaw members are arranged to receive surgical energy from a surgical generator. The tissue engaging portion further includes at least one cooling member spaced from at least one of the first and second jaw members, where the cooling member has an open position and a closed position for engaging the tissue. Positioning the jaw members in their closed position and applying surgical energy to the tissue allows for treatment of the tissue, and positioning the cooling member in its closed position provides at least one of a pressure gradient or a thermal gradient between the jaw members and the cooling member.

21 Claims, 4 Drawing Sheets

U.S. PATENT DOCUMENTS

| | | |
|---|---|---|
| 6,623,482 B2 | 9/2003 | Pendekanti et al. |
| 6,652,521 B2 | 11/2003 | Schulze |
| 6,676,660 B2 | 1/2004 | Wampler et al. |
| 6,695,840 B2 | 2/2004 | Schulze |
| 6,773,435 B2 | 8/2004 | Schulze et al. |
| 6,780,180 B1 | 8/2004 | Goble et al. |
| 6,790,217 B2 | 9/2004 | Schulze et al. |
| 6,832,998 B2 | 12/2004 | Goble |
| 6,849,075 B2 | 2/2005 | Bertolero et al. |
| 6,971,395 B2 | 12/2005 | Edwards et al. |
| 2003/0120268 A1* | 6/2003 | Bertolero et al. ............... 606/32 |
| 2003/0125604 A1* | 7/2003 | Kochamba et al. ............ 600/37 |
| 2003/0216733 A1* | 11/2003 | McClurken et al. ........... 606/51 |
| 2006/0052778 A1* | 3/2006 | Chapman et al. ............... 606/51 |

\* cited by examiner

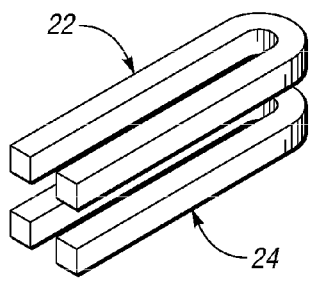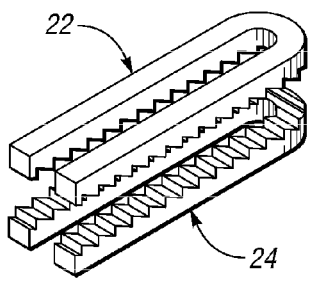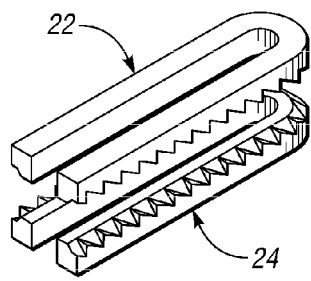
Fig. 3          Fig. 4          Fig. 5
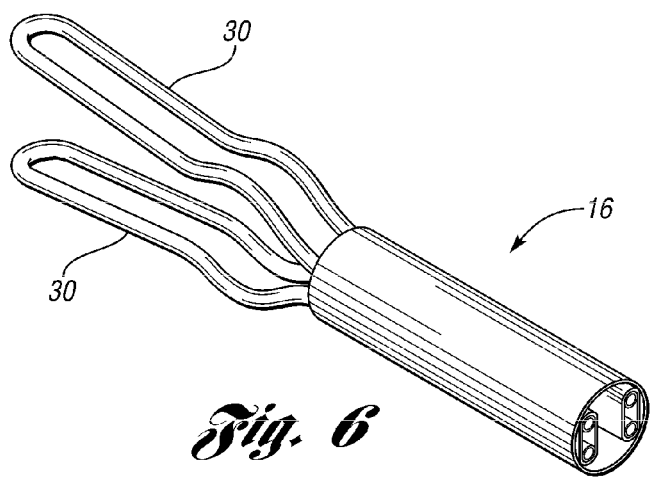
Fig. 6
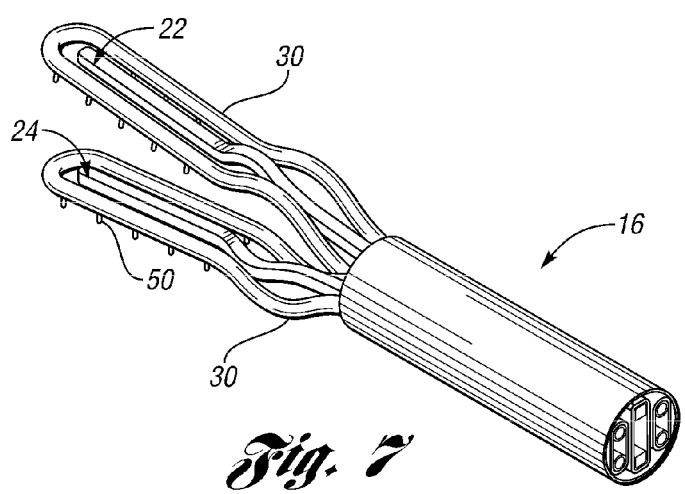
Fig. 7

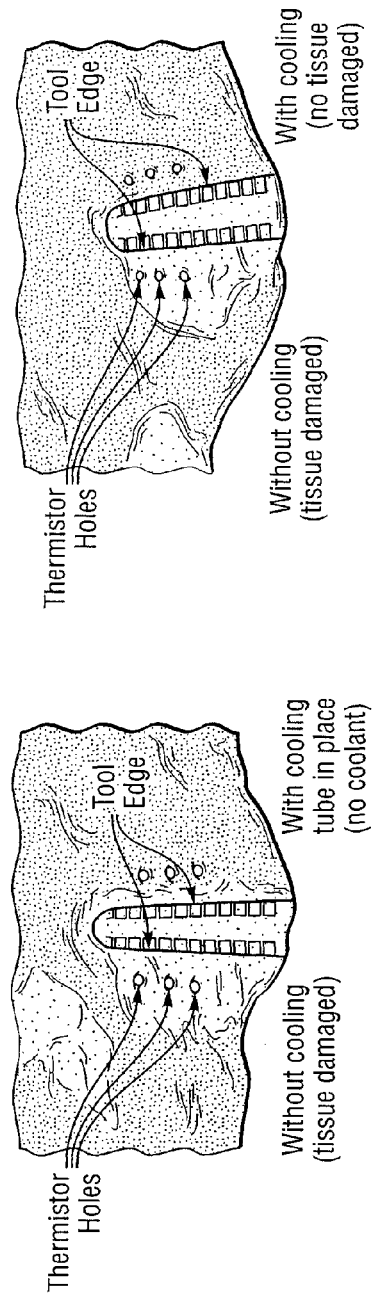
Fig. 11
Fig. 12
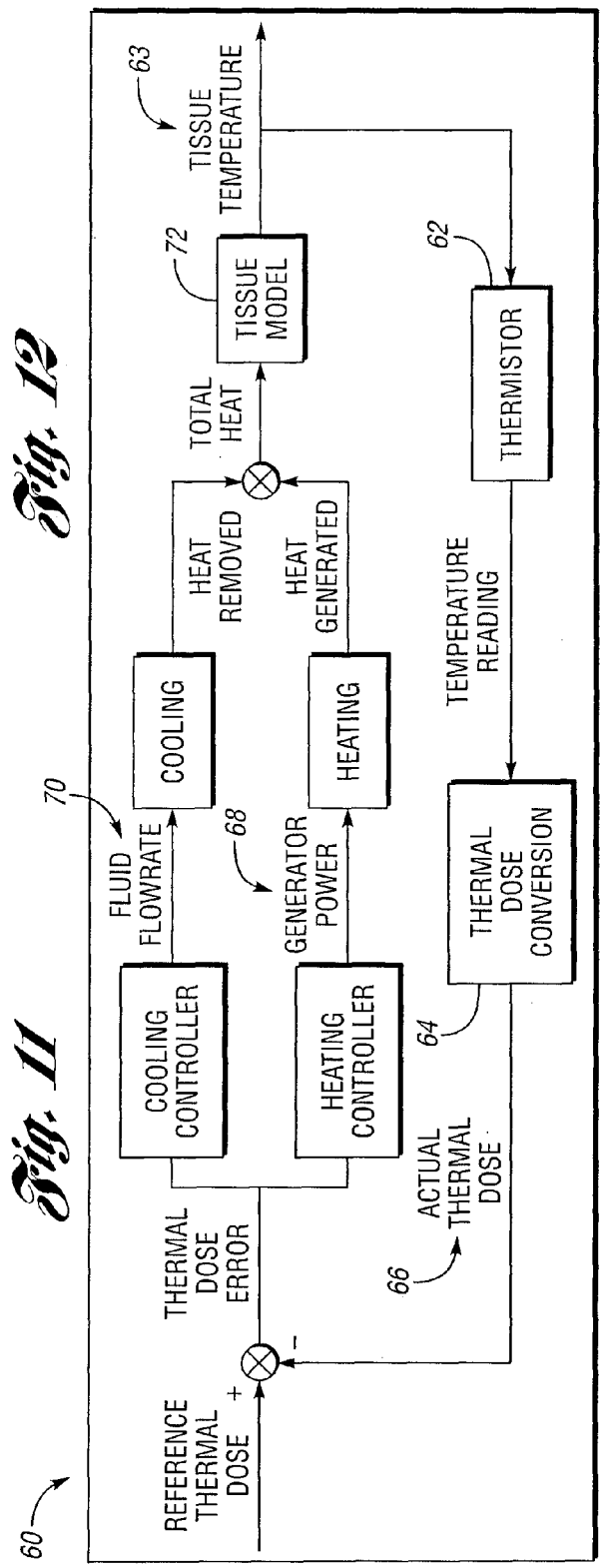
Fig. 13

SURGICAL INSTRUMENT AND METHOD FOR USE THEREOF

CROSS-REFERENCE TO RELATED APPLICATIONS

This application claims the benefit of U.S. provisional application Ser. No. 60/761,901 filed Jan. 25, 2006, which is incorporated by reference herein.

BACKGROUND OF THE INVENTION

1. Field of the Invention

This invention relates to a surgical instrument, such as an energy based surgical device.

2. Background Art

Energy-based surgical devices (EBSDs), which use a variety of energy sources (electrical, radio frequency, and ultrasonic), have been adopted widely for nearly all types of surgery due to their ability to effectively and rapidly control bleeding. EBSDs have been adopted widely for nearly all types of surgery including neurosurgery, orthopedics, gynecology, urology, general surgery, thoracic surgery, plastic surgery, and otolaryngology. Despite their advantages, the success of EBSDs has been tempered by the recognition that these devices can lead to collateral tissue damage due to thermal and/or electrical spread outward from the instrument.

For example, electrosurgery (monopolar and bipolar) involves the use of alternating current in the radio frequency (RF) range to generate heat for cutting and coagulating tissue. In bipolar electrosurgery, opposed grasping members are used to clamp tissue therebetween for coagulation, wherein the grasping members comprise electrodes of opposite polarity. As electrical energy passing through the tissue is transformed into heat, the tissue is desiccated and the loss of water produces an increased electrical resistance. As a result, surrounding tissue becomes relatively less resistive to electrical current and the current's pathway will switch course, resulting in a spread of thermal energy to tissue outside of the grasping members. This makes predicting the route current will take very difficult and not intuitive, and may lead to unintentionally damaging nearby tissue.

In addition, medical personnel may not always be able to visualize the thermal spreading because of obstructing tissue structures, especially during an endoscopic procedure. The limited field of view and narrow focus on a small area may allow thermal spread to occur unnoticed, potentially causing damage to vital structures. When performing electrosurgery or ultrasurgery in a laparoscopic environment, the presence of an insufflating gas having a low heat capacity may result in instruments not cooling as rapidly, which may further increase the potential for thermal damage.

Therefore, it is desirable to control the thermal spread from EBSDs in order to minimize unwanted thermal damage to surrounding tissues during surgical procedures as well as reduce patient recovery times and post-operative complications.

BRIEF DESCRIPTION OF THE DRAWINGS

FIG. 3 is a perspective view of a smooth electrode configuration according to one aspect of the present invention;

FIG. 4 is a perspective view of a toothed electrode configuration according to another aspect of the present invention;

FIG. 5 is a perspective view of a hybrid electrode configuration having both smooth areas and toothed areas according to another aspect of the present invention;

FIG. 6 is a perspective view of a tissue engaging portion wherein cooling members serve as electrodes according to an aspect of the present invention;

FIG. 7 is a perspective view of a tissue engaging portion which includes temperature sensors according to an aspect of the present invention;

FIG. 11 is an illustration of an example of the experimental group in which a cooling tube was placed but did not contain coolant;

FIG. 12 is an illustration of an example of the experimental group in which a cooling tube was placed and contained coolant; and FIG. 13 is a schematic representation of a control system according to an aspect of the present invention.

DETAILED DESCRIPTION OF THE INVENTION

As required, detailed embodiments of the present invention are disclosed herein; however, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a representative basis for teaching one skilled in the art to variously employ the present invention.

The present invention includes a surgical instrument and method for use thereof for controlling, minimizing, and monitoring the spread of thermal energy during any type of surgery. In accordance with the present invention, thermal and/or pressure gradients may be created in the treated tissue to alleviate thermal spread.

Figure 1:
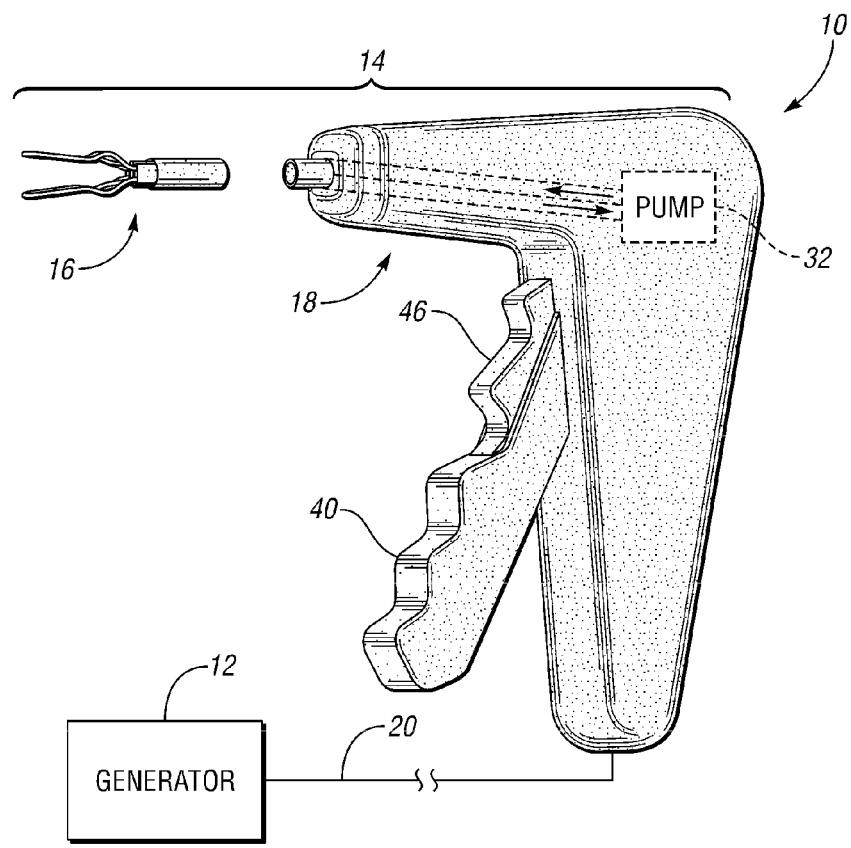
FIG. 1 is a perspective view of a surgical instrument system according to an aspect of the present invention.

A perspective view of a surgical instrument system according to the present invention is shown in FIG. 1 and designated generally by reference numeral 10. System 10 includes a surgical energy generator 12 such as, but not limited to, a monopolar electrosurgical generator, a bipolar electrosurgical generator, or an ultrasonic generator. Electrosurgical generators are microprocessor-controlled electrical generators that deliver power in the form of the necessary waveforms. Ultrasonic generators are microprocessor-controlled and supply high frequency pulses of alternating current to the handpiece, which in turn vibrates the transducer. Monopolar devices include, for example, the Surgistat® and Force FX generators manufactured by Valleylab (Boulder, Colo.). Bipolar devices include, for example, the LigaSure™ Vessel Sealing System from Valleylab and the PK™ System from Gyrus Medical (Maple Grove, Minn.). Ultrasonic devices include, for example, Harmonic Scalpel® by Ethicon Endo-Surgery, Inc. (Cincinnati, Ohio), AutoSonix® by Tyco Healthcare (Norwalk, Conn.), and SonoSurg® by Olympus Corp. (Melville, N.Y.).

With continued reference to FIG. 1, system 10 according to the present invention includes an energy based surgical instrument 14 comprising a tissue engaging portion 16 and a handpiece 18 arranged to removably receive portion 16. Handpiece 18 may have a pistol-grip style as depicted herein, but is not limited to this configuration. Tissue engaging portion 16 is arranged to be connected to handpiece 18 both mechanically and electrically, and cable 20 may be provided to connect instrument 14 to generator 12. Activation of generator 12 may be performed from handpiece 18 or by means of a footswitch unit (not shown) as is known in the art. Surgical energy, such as electrosurgical or ultrasonic energy, may then be conducted to instrument 14 and the tissue treated to a desired degree.

Figure 2:
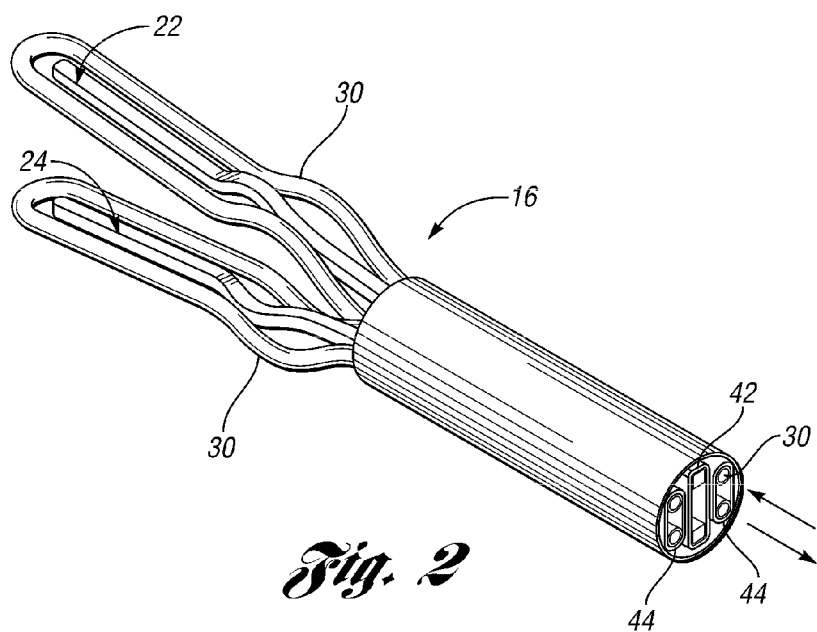
FIG. 2 is a perspective view of a tissue engaging portion of a surgical instrument according to an aspect of the present invention.

Tissue engaging portion 16 may have a configuration as depicted in FIG. 2, wherein portion 16 includes a first jaw member 22 and an opposed second jaw member 24 which are movable relative to one another. Jaw members 22, 24 may be positioned in a spaced apart, open position as shown in FIG. 2 for receiving tissue therebetween, and jaw members 22, 24 may be positioned in a closed position where jaw members 22, 24 are moved relatively closer to one another in order to engage and treat the tissue therebetween. Jaw members 22, 24 may have an arm-like configuration as depicted in FIGS. 1 and 2. However, as shown in FIGS. 3-5, numerous configurations of jaw members 22, 24 are contemplated according to the present invention. Jaw members 22, 24 may have a U-shaped configuration and could have smooth surfaces (FIG. 3), could have toothed surfaces (FIG. 4), or could have a combination of smooth and toothed surfaces (FIG. 5). It is understood that jaw members 22, 24 are not limited to the shape, size, and other configuration depicted herein, and that any configuration of jaw members 22, 24 suitable for the intended purpose is fully contemplated. Furthermore, instrument 14 may also include a cutting element if desired.

Jaw members 22, 24 are arranged to receive surgical energy from surgical generator 12. In the case of a bipolar electrosurgical instrument, first jaw member 22 comprises a first electrode and second jaw member 24 comprises a second electrode, wherein the first and second electrodes have opposite polarity to allow current to flow therebetween. The electrodes may be constructed from a conductive material such as, but not limited to, aluminum, stainless steel, platinum, silver, or gold. Although instrument 14 may sometimes be described herein as being a bipolar electrosurgical instrument, it is understood that embodying instrument 14 as a monopolar electrosurgical device, ultrasonic surgical device, or other energy based surgical device is fully contemplated according to the present invention.

Instrument 14 may be used to dissect, grasp or clamp, coagulate, and cut tissues during endoscopic, laparoscopic, and open surgical procedures. Instrument 14 may be designed for single patient use, or may be constructed to allow for sterilization and use on more than one surgical patient.

As described above, during electrosurgical or ultrasonic procedures, the thermal spread or dissipation of heat outside the tissue area engaged by tissue engaging portion 16 may occur. As best shown in FIG. 2, tissue engaging portion 16 may further include at least one cooling member 30 spaced from at least one of first jaw member 22 and second jaw member 24. In the configuration depicted herein, one cooling member 30 is spaced from and generally surrounding jaw member 22, and another cooling member 30 is spaced from and generally surrounding jaw member 24. Cooling members 30 may each comprise a tube which may be U-shaped as depicted in FIG. 2. Of course, it is understood that other numbers and configurations of cooling member 30 are fully contemplated. As with jaw members 22, 24, cooling member (s) 30 are movable relative to one another and may be positioned in an open position (FIG. 2) and a closed position for engaging tissue. As heat is introduced into the tissue by surgical instrument 14, cooling members 30 may constrain the thermal spread by increasing the pressure and/or temperature gradient in the heated region as described below.

Cooling members 30 may include a coolant such as water or any other suitable liquid, chilled or unchilled, where the coolant may be stationary or may be circulated within cooling members 30 (see, for example, arrows in FIG. 2) by a pump 32 (shown schematically in FIG. 1) housed in handpiece 16 or elsewhere, or by other means. In operation, as heat is generated at jaw members 22, 24, the coolant is also heated and that heat may be taken away from the adjacent tissue by fluid flow toward handpiece 18. According to an aspect of the present invention, cooling member 30 adjacent jaw member 22 may have a different flow direction compared with cooling member 30 adjacent jaw member 24. The coolant may be supplied and/or circulated within cooling members 30 before, during, and/or after the surgical procedure. Instead of a liquid such as water, cooling member 30 could contain a gas coolant, such as carbon dioxide. Still further, cooling member 30 could impart a Peltier effect by supplying current to pull heat away from the tissue.

According to another aspect of the present invention, cooling member 30 may comprise a heat pipe. In this case, cooling member 30 may include a tube or other member containing a low boiling temperature liquid, such as acetone or alcohol. In use, heat from jaw members 22, 24 causes the liquid within a distal end of the tube (toward portion 16) to vaporize, and this vapor may subsequently condense at a proximal end of the tube (toward handpiece 18) due to its relatively cooler temperature with respect to the distal end. In this way, heat may transferred from the distal end of instrument 14 to the proximal end and away from the treated tissue.

Cooling members 30 may be constructed of aluminum, stainless steel, or any other suitable electrically conductive or non-conductive material. With reference to FIG. 6, if constructed from an electrically conductive material, cooling members 30 themselves could actually function as electrodes without the need for jaw members 22, 24. Cooling members 30 may then be arranged to receive surgical energy from generator 12 for treating tissue, and may contain a coolant therein which may be activated before, during, and/or after the application of surgical energy. Again, the size, shape, and overall configuration of cooling members 30 is not limited to that depicted herein.

In the case of an electrosurgical device, application of cooling member 30 may result in the 'pigeon-holing' of the electrical energy, focusing it on the tissue of interest. Meanwhile, the increased thermal resistance allows cooling member 30 to more effectively conduct the thermal energy from the tissue while the coolant may convect it away from the surgical area, thereby decreasing the temperature of the tissue. Instrument 14 according to the present invention may not only perform the surgical procedure more effectively, but due to the concentration of electrical energy, may perform it more efficiently as well. In the case of an ultrasonic device, where friction represents the main component of thermal energy production, cooling member 30 may again increase the local thermal resistance of the tissue, allowing cooling member 30 to more effectively conduct the thermal energy from the tissue while the coolant may convect it away from the surgical area.

With reference again to FIGS. 1 and 2, handpiece 18 may include a first actuator 40 for closing and opening jaw members 22, 24 to engage or release tissue therebetween. Proximal portions of jaw members 22, 24 are disposed within a sheath 42 which is operably connected to actuator 40 to allow for mechanical actuation of jaw members 22, 24 via proximal and distal movement of sheath 42 as is known in the art. Of course, any other mechanism for opening and closing jaw members 22, 24 is also fully contemplated. First actuator 40 may also control the opening and closing of cooling members 30 via movement of sheath 44 using a similar mechanism, wherein the opening and closing of cooling members 30 and jaw members 22, 24 may be synchronized. Alternatively, handpiece 18 may include a second actuator 46 for mechanical actuation of cooling members 30. With second actuator 46, cooling members 30 may be actuated to engage and compress tissue before, after, or simultaneous with jaw members 22, 24, and may be actuated to release tissue before, after or simultaneous with jaw members 22, 24.

First actuator 40 and/or second actuator 46 may include a return spring or other means for providing a biasing force to the open position of jaw members 22, 24 and/or cooling members 30. First actuator 40 and/or second actuator 46 could also include a releasable locking mechanism such that constant depression of either actuator 40 or 46 would not be required to maintain the closed position of jaw members 22, 24 and/or cooling members 30. Furthermore, the operation of first actuator 40 and second actuator 46 could be dependent upon one another such that, for example, depression of second actuator 46 to move cooling members 30 to the closed position would need to occur before first actuator 40 could be depressed.

Whether controlled by first actuator 40 or second actuator 46, cooling members 30 may be arranged to apply a greater compressive pressure on the tissue in their closed position compared with the pressure applied by the clamping of jaw members 22, 24 in their closed position. In this way, an increased pressure gradient may be induced on the tissue. Such a gradient may effectively increase both the thermal and electrical resistance of the tissue. Pressure applied by cooling members 30 alone, without use of a coolant therein, is fully contemplated according to the present invention. Therefore, application of cooling member 30 may provide at least one of a pressure gradient or a thermal gradient between cooling member 30 and jaw members 22, 24 to control thermal spread during energy based surgical procedures, such as electrosurgery or ultrasonic surgery.

As shown in FIG. 7, temperature sensors 50, such as thermistors, may be provided on cooling members 30, jaw members 22, 24, or another area of tissue engaging portion 16 to provide real-time, internal in vivo tissue temperature measurement during surgical procedures.

Figure 8:
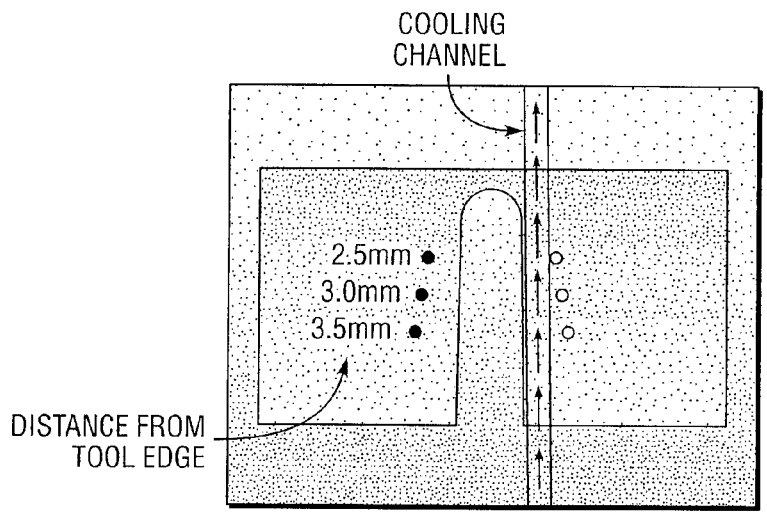
FIG. 8 is a schematic diagram of an experimental set-up wherein a cooling tube was placed adjacent the jaw members and temperatures recorded at different distances from the edge of the jaw members.

In order to demonstrate the effectiveness of a cooling member 30 according to the present invention, several experiments were performed. With reference to FIG. 8, commercially available ex-vivo chicken tissue and bipolar electrosurgery was used to test the effects of a cooling channel placed alongside a surgical instrument during coagulative surgical procedures. An Instech P625 Peristaltic Pump with 0.093" ID tubing was used to flow chilled water through the cooling channel at a flow rate of 3.3 mL/min. Both SS 304 and Al 3003 were used as cooling channels.

The bite size for the surgical procedures was limited to ¾ of the jaw length to avoid variations in tissue effect at the jaw hinge area. Lateral tension to the tissue was avoided to ensure effects were limited to the devices. The tissue temperature was measured on both sides of the electrosurgical tool at a depth of 2.0 mm under the tissue surface using thermistors placed at 2.5, 3.0, and 3.5 mm from the tool edge. Polycarbonate fixtures were created for the device tested to ensure temperature measurements were recorded at precise distances from the tool edge (see FIG. 8). Upon tissue clamping, the fixture was placed around the device and held lightly in place while the trials proceeded.

Figure 10:
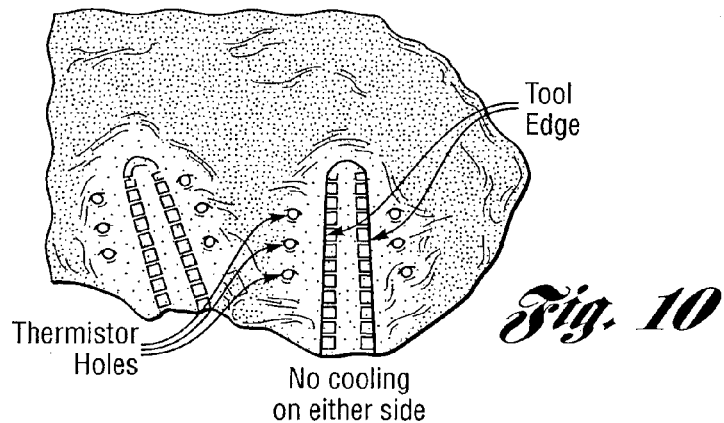
FIG. 10 is an illustration of an example of the experimental control group in which a cooling tube was not used.

The following scenarios were tested: (1) no cooling channel in place (control), (2) SS cooling channel in place with no coolant, (3) Al cooling channel in place with coolant, and (4) SS cooling channel in place with coolant. In the control group, the average ratio of temperatures from the left side of the tool to the right side tool (FIG. 8) at 2.5 mm, 3.0 mm, and 3.5 mm away from the tool edge was 1.14, 0.99, and 1.05 with a standard deviation of 0.12, 0.12, and 0.12 respectively, where an exemplary illustration of the results of this trial is shown in FIG. 10.

Figure 9:
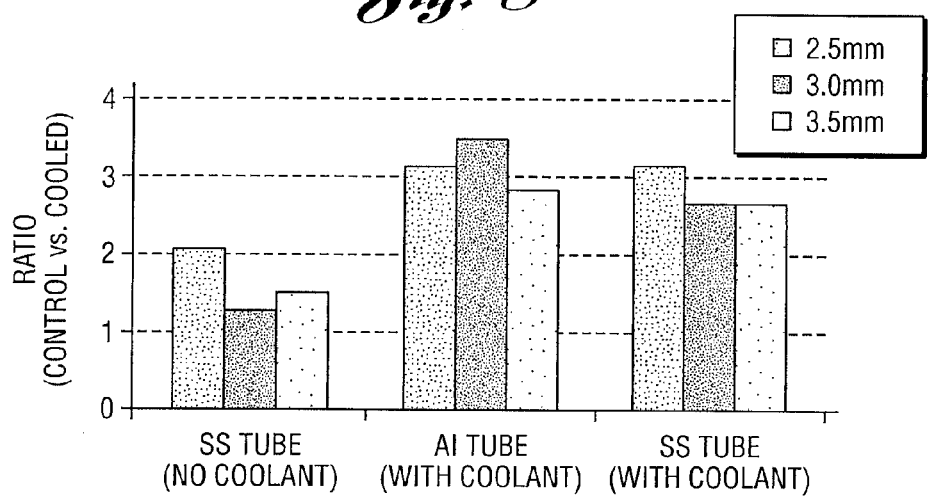
FIG. 9 is a graph depicting the experimental results using a cooling tube with and without coolant.

With reference to FIGS. 9 and 11, for group (2) the average ratio of temperatures from the left side (no cooling channel) to the right side (cooling channel without coolant) at 2.5 mm, 3.0 mm, and 3.5 mm away from the tool edge was 2.08, 1.31, and 1.54 with a standard deviation of 0.54, 0.52, and 0.51 respectively. With reference to FIGS. 9 and 12, for group (3) the average ratio of temperatures from the left side (no cooling channel) to the right side (cooling channel with coolant) at 2.5 mm, 3.0 mm, and 3.5 mm away from the tool edge was 3.13, 3.47, and 2.82 with a standard deviation of 1.22, 2.56, and 1.26 respectively. For group (4), the average ratio of temperatures from the left side (no cooling channel) to the right side (cooling channel with coolant) at 2.5 mm, 3.0 mm, and 3.5 mm away from the tool edge was 3.12, 2.64, and 2.84 with a standard deviation of 1.26, 0.89, and 0.79 respectively.

Therefore, data collected indicates a much lower temperature realized for tissue being actively cooled compared to tissue left thermally untreated. Use of the cooling member showed adequate tissue temperature reduction in tissue as close as 2.5 mm from the tool edge to avoid permanent thermal damage at those distances. As shown in FIG. 11, the high thermal gradients created near the right side of the surgical device resulted in much less thermal spread for the case of a SS304 cooling tube without coolant being positioned next to the device, and was almost completely eliminated when coolant flowing at 3.3 mL/min was passed through either an Al3003 or SS304 cooling channel as demonstrated in FIG. 12.

The results obtained from actively cooling local tissue during electrosurgical procedures demonstrate the ability to minimize and possibly eliminate the thermal spread associated with surgical tools that rely on the production of heat to coagulate and/or cut tissue. The reduction in thermal spread seen simply with the application of the cooling member suggests that even the modest pressure placed on the tissue by the tube increases both the thermal and electrical resistance of the tissue. The significantly increased thermal conductivity of the tube over the tissue (~0.5 W/mK) may allow the cooling member to conduct most of the heat that would normally be retained by the tissue resulting in increasing tissue temperature. The addition of coolant flowing through the tube allows the convective qualities of the coolant to convect the heat conducted by the cooling member and transmit it away from the surgical site. By maintaining the cooling member at as low a temperature as possible, a high thermal gradient may be created allowing for maximum heat conduction by the cooling member.

In further accordance with the present invention, FIG. 13 depicts a control system 60 for controlling the temperature distribution within the treated tissue. Control system 60 may use temperature sensors such as thermistors 62 placed locally in sensitive tissue to monitor the tissue temperature 63 in real-time during surgery. Algorithms may be used to convert 64 the temperature to a thermal dose so as to continuously monitor the thermal dose 66 the tissue has absorbed. This data may serve as an input in control system 60 where both the power 68 output by surgical generator 12 as well as the flow rate 70 of coolant within cooling member 30 may be controlled by that input. In addition, a tissue model 72 may be utilized for predicting and controlling tissue heating, which may be helpful in areas hard to reach by temperature sensors, such as in brain or spinal electrosurgery. Inputs of tissue model 72 may include tissue type, electrode type, presence of cooling member 30, tissue resistance (determined, for example, via a pressure sensor or tissue thickness), and others, where model 72 may be used to predict the temperature gradient, resulting thermal dose, and surgical time for the treated tissue area.

For example, cooling member 30 could be modeled as a circular pipe with constant wall heat flux. Assuming fully developed flow has been established the non-dimensionalized governing equation becomes:

$$T(x, r) = T_{as}(r) + T_{en}(x, r)$$

where $$T_{as} = C_0 + C_1 x + \theta(r),$$

$\theta(r)$=centerline temperature and $T_{en}$ is a Sturm-Louiville problem in r with BC of constant heat flux.

Using the power output from generator 12 as another input along with the material properties of the tissue, cooling member 30, and coolant, the temperature of the tissue at discrete distances from tissue engaging portion 16 may be determined. Also, in surgical practice, the temperature gradient of the coolant could be used as a control input if the distance from instrument 16 is known. If this is so, tissue temperature could be monitored indirectly through the coolant.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A surgical instrument for treating a tissue, comprising:
   a handpiece; and
   a tissue engaging portion arranged to be received by the handpiece, the tissue engaging portion comprising
      first and second opposed jaw members having an open position and a closed position for engaging the tissue therebetween, the first and second jaw members arranged to receive surgical energy from a surgical generator, and
      at least one cooling member spaced from at least one of the first and second jaw members, the at least one cooling member separately movable with respect to the jaw members and having an open position and a closed position for engaging the tissue,
   wherein positioning the jaw members in their closed position and applying surgical energy to the tissue allows for treatment of the tissue, and positioning the at least one cooling member in its closed position provides at least one of a pressure gradient or a thermal gradient between the jaw members and the at least one cooling member.

2. The surgical instrument according to claim 1, wherein the jaw members have an arm-like configuration.

3. The surgical instrument according to claim 1, wherein the jaw members have a U-shaped configuration.

4. The surgical instrument according to claim 1, wherein the first jaw member comprises a first electrode and the second jaw member comprises a second electrode of opposite polarity from the first electrode.

5. The surgical instrument according to claim 1, wherein the at least one cooling member comprises a first cooling member generally surrounding the first jaw member and a second cooling member generally surrounding the second jaw member.

6. The surgical instrument according to claim 1, further comprising a first actuator operably connected to the first and second jaw members for effecting movement thereof.

7. The surgical instrument according to claim 6, wherein the first actuator is operably connected to the at least one cooling member for effecting movement thereof.

8. The surgical instrument according to claim 6, further comprising a second actuator operably connected to the at least one cooling member for effecting movement thereof.

9. The surgical instrument according to claim 1, wherein the at least one cooling member contains a coolant.

10. The surgical instrument according to claim 9, further comprising a pump in communication with the at least one cooling member for circulating the coolant therethrough.

11. The surgical instrument according to claim 1, wherein the at least one cooling member comprises a heat pipe.

12. The surgical instrument according to claim 1, wherein the at least one cooling member imparts a Peltier effect.

13. The surgical instrument according to claim 1, further comprising at least one temperature sensor provided on the tissue engaging portion.

14. An electrosurgical system, comprising:
   a handpiece;
   a tissue engaging portion arranged to be received by the handpiece, the tissue engaging portion comprising
      first and second opposed electrodes of opposite polarity, the electrodes having an open position and a closed position for engaging the tissue therebetween, and
      cooling members spaced from and generally surrounding each electrode, the cooling members separately movable with respect to the electrodes and having an open position and a closed position for engaging the tissue; and
   an electrosurgical generator for supplying radio frequency energy to the electrodes,
   wherein positioning the electrodes in their closed position and applying energy to the tissue allows for treatment of the tissue, and positioning the cooling members in their closed position provides at least one of a pressure gradient or a thermal gradient between the electrodes and the cooling members.

15. A method for treating a tissue, comprising:
   providing a surgical instrument comprising a handpiece and a tissue engaging portion arranged to be received by the handpiece, the tissue engaging portion comprising first and second opposed jaw members having an open position and a closed position for engaging the tissue therebetween, the first and second jaw members arranged to receive surgical energy from a surgical generator, and at least one cooling member spaced from at least one of the first and second jaw members, the at least one cooling member separately movable with respect to the jaw members and having an open position and a closed position for engaging the tissue;
   positioning the jaw members in their closed position and applying surgical energy to the tissue; and positioning the at least one cooling member in its closed position to provide at least one of a pressure gradient or a thermal gradient between the jaw members and the at least one cooling member.

16. The method according to claim 15, wherein positioning the jaw members in their closed position and positioning the at least one cooling member in its closed position occurs at approximately the same time.

17. The method according to claim 15, wherein positioning the at least one cooling member in its closed position occurs prior to positioning the jaw members in their closed position.

18. The method according to claim 15, further comprising providing a coolant within the at least one cooling member.

19. The method according to claim 18, further comprising circulating the coolant through the at least one cooling member.

20. The method according to claim 19, wherein the at least one cooling member comprises a first cooling member generally surrounding the first jaw member and a second cooling member generally surrounding the second jaw member, wherein circulating the coolant includes circulating the coolant through the first and second cooling members in different flow directions.

21. The method according to claim 15, further comprising sensing a temperature adjacent the tissue engaging portion.

* * * * *